United States Patent [19]

Raghu et al.

[11] 4,090,025
[45] May 16, 1978

[54] INTERMEDIATES FOR SYNTHESIS OF TETRAMISOLE, LEVAMISOLE AND THEIR DERIVATIVES

[75] Inventors: Sivaraman Raghu, Norwalk; Arthur Kentaro Hoffmann, New Canaan; Balwant Singh, Stamford, all of Conn.

[73] Assignee: American Cyanamid Company, Stamford, Conn.

[21] Appl. No.: 739,924

[22] Filed: Nov. 8, 1976

Related U.S. Application Data

[63] Continuation-in-part of Ser. No. 680,311, Apr. 26, 1973, abandoned.

[51] Int. Cl.$^2$ ............... C07D 233/32; C07D 233/38; C07D 233/42
[52] U.S. Cl. .................. 548/320; 260/306.7 T; 260/307 F; 260/570.5 C
[58] Field of Search ............ 260/309.7; 548/320

[56] References Cited

U.S. PATENT DOCUMENTS 3,726,894  4/1973  Spicer ............... 260/309.7

OTHER PUBLICATIONS

Fieser et al. Advanced Organic Chemistry pp. 73–78, N.Y. Reinhold, 1961.
Rodionov et al. Chem. Abst. 1949, vol. 43, Column 3821.
Kametani Chem. Abst. 1952, vol. 46, columns 4547–4548.

*Primary Examiner*—Natalie Trousof
*Attorney, Agent, or Firm*—Norton S. Johnson

[57] ABSTRACT

A process for the manufacture of 1-(2-alkoxyethyl)-4-phenyl-4-imidazolin-2-ones, 1-(2-alkoxyethyl)-4-phenyl-2-imidazolidones, 1-(2-alkoxyethyl)-4-phenyl-imidazolidine-2-thiones, certain of the corresponding 1-(2-hydroxyethyl) derivatives and their 3-acylated derivatives, and certain related compounds which are all useful as intermediates in a new process for the manufacture of tetramisole, dl-2,3,5,6-tetrahydro-6-phenylimidazo-[2,1-b]thiazole, and its derivatives. The compound tetramisole is useful as an anthelmintic.

26 Claims, No Drawings

INTERMEDIATES FOR SYNTHESIS OF TETRAMISOLE, LEVAMISOLE AND THEIR DERIVATIVES

BACKGROUND OF THE INVENTION

There are several procedures for the production of the anthelmintic tetramisole reported in the literature (Raemaekers et al., J. Med. Chem. 9, 545 (1966), Bakelien et al., Aust. J. Chem. 21 1557 (1968), T. R. Roy, U.S. Pat. No. 3,855,234, M. E. McMenin, U.S. Pat. No. 3,845,070). The Raemaekers method involves a reduction step involving sodium borohydride, an expensive reducing agent. The process in U.S. Pat. No. 3,855,234 suffers from lack of regioselectivity and also from problems of isolation of intermediates.

A method for making tetramisole from 1-(2-hydroxyethyl)-4-phenyl-4-imidazolin-2-thione and thionyl chloride is disclosed in U.S. Pat. No. 3,726,894. This compound is made by the hydroboration reaction on 1-vinyl-4-phenyl-4-imidazolin-2-thione.

The literature also reports two methods for the synthesis of levamisole, the levorotatory isomer of tetramisole, without its resolution (Raemaekers et al., Tetrahedron Letters, 1467 (1967) and P. R. Dick, French Patent 2224-472). However, these procedures are not regioselective in that they would also produce some "isotetramisole", (2,3,5,6-tetrahydro-4-phenylimidazo(2,1-b)thiazole), which would have to be separated. No mention of this separation has been made in the above publication.

The instant invention overcomes all these drawbacks in that it is regioselective (no isotetramisole can be formed); all the steps occur in good yields and the intermediates are easy to isolate; it involves for the first time in tetramisole synthesis a catalytic reduction step; and it is applicable to the synthesis of other analogs.

FIELD OF THE INVENTION

The instant invention relates to the synthesis of 1,4-disubstituted 4-imidazolin-2-ones, 1,4-disubstituted imidazolidin-2-ones, 1,4-disubstituted imidazolidine-2-thiones and certain of their 3-acylated derivatives and their subsequent conversion to tetramisole or substituted tetramisoles.

SUMMARY OF THE INVENTION

The instant invention relates to a novel process, using novel intermediates, for the production of tetramisole. It involves simpler and fewer steps and is capable of producing the appropriate pharmaceutically acceptable acid-addition salts of tetramisole directly. The instant invention is also applicable to other analogs of tetramisole.

The instant invention is based on the synthesis of the catalytically reducible, appropriately substituted imidazolinone (IV) or derivative. This is achieved by reaction of the α-substituted ketone (I) with an amine such as (II) to give the intermediate α-(2-substituted ethyl)aminoketone (III).

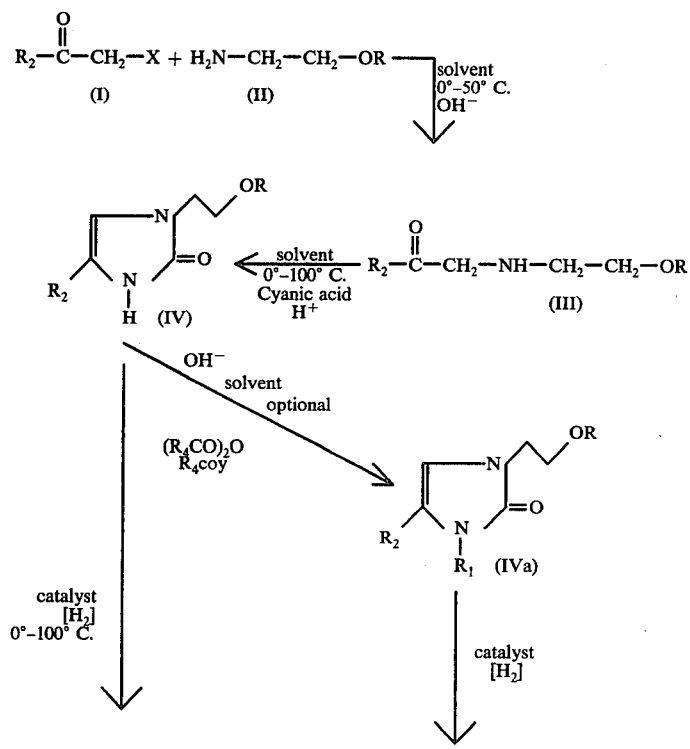

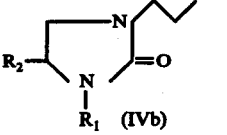

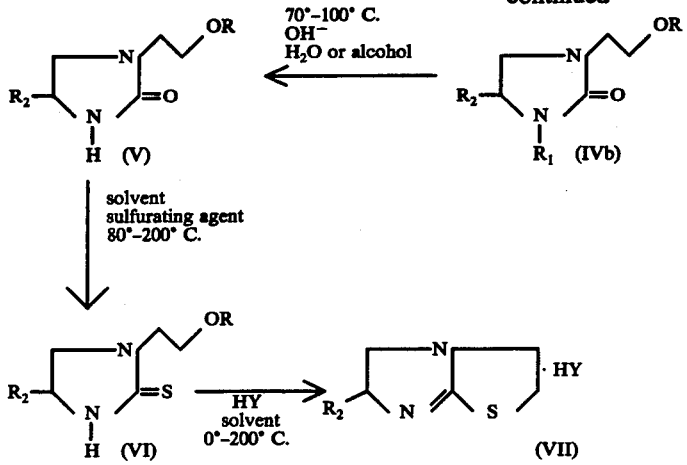

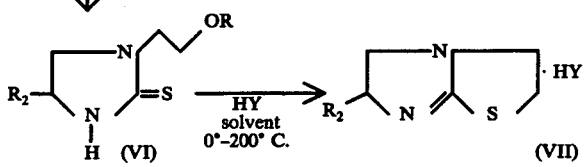

(R, $R_1$, $R_2$, $R_3$, X and Y are defined on the following pages)

An α-substituted ketone of formula I, wherein $R_2$ is selected from the group consisting of phenyl and phenyl substituted with up to two groups selected from the group consisting of lower alkyl, lower alkoxy, halo, and trifluoromethyl, and X is a group (such as chlorine, fluorine, bromine, iodine and p-toluenesulfonate) which can be displaced by a nucleophilic reagent, is reacted with an amine of formula II or its acid addition salts, wherein R is selected from the group consisting of hydrogen, $C_1$–$C_6$ alkyl, halo $C_1$–$C_6$ alkyl, and phenyl, optionally substituted with up to three group selected from the group consisting of lower alkyl, halo and lower alkoxy, and a moiety of the formula $COR_3$, wherein $R_3$ is selected from the group consisting of hydrogen, $C_1$–$C_6$ alkyl, halo $C_1$–$C_6$ alkyl, phenyl and phenyl substituted with up to four groups selected from the group consisting of lower alkyl, halo, lower alkoxy and trifluoromethyl; to yield the compound of formula III. This reaction can be run using an excess of the compound of formula II, or in the presence of a tertiary amino such as triethylamine, or in the presence of a hydroxide source such as sodium carbonate, at a temperature from about 0° to about 50° C. in a solvent (such as alcohol or halocarbon) from about 30 minutes to about 3 hours.

Compound III (wherein $R_2$ is phenyl or phenyl substituted with up to two groups selected from the group consisting of lower alkyl, lower alkoxy, halo and trifluoromethyl and R is as defined for Compound II above) is dissolved in any suitable organic solvent (such as methanol, chloroform or methylene chloride), heated from about 0° to about 100° C. in the presence of cyanic acid and a suitable hydronium ion source to yield the imidazolinone of formula IV.

Two alternative routes for the production of the imidazolidone of formula V are feasible. In the first of these two routes the imidazolinone of formula IV (wherein $R_2$ is phenyl or phenyl substituted with up to two groups selected from the group consisting of lower alkyl, lower alkoxy, halo and trifluoromethyl and R is defined as for Compound II above) is hydrogenated at about 15 to about 1000 psig of hydrogen in a suitable solvent (such as alcohol, hydrocarbon, mixed alcohol-hydrocarbon solvent or acetic acid) in the presence of a catalyst (such as palladium or platinum on a suitable solid support, or a homogeneous catalyst) at a temperature from about 0° to about 100° C. for about 30 minutes or more, or reduced with a suitable reducing agent, to yield the imidazolidone of formula V. In the second of these two routes the imidazolinone of formula IV is reacted with an acyl halide or acyl anhydride of the formula:

$$R_4COY \text{ or } (R_4CO)_2O$$

wherein $R_4$ is selected from the group consisting of $C_1$–$C_6$ alkyl, $C_1$–$C_6$ alkoxy, phenoxy, $C_5$–$C_{10}$ cycloalkyl, phenyl, and phenyl or phenoxy substituted with up to four groups selected from the group consisting of lower alkyl, lower alkoxy, halo and trifluoromethyl, and Y is any group (such as halogen) which can be displaced by a nucleophilic reagent, in the presence of a hydroxide ion source while refluxing neat or in a hydrocarbon solvent to yield the imidazolinone of formula IVa. The imidazolinone of the formula IVa (wherein $R_1$ and $R_2$ are as defined above and $R_1$ is $R_4CO$ wherein $R_4$ is as defined above) is hydrogenated under the same conditions for IV→V to yield the imidazolidone of formula IVb. In the course of the hydrogenation of either IV or IVa, any halogens that may be present as part of the R, $R_1$, or $R_2$ groups will be removed and replaced by hydrogen unless mild conditions of hydrogenation or other reduction are used. The imidazolidone of formula IVb is hydrolyzed in the presence of a hydroxide ion source in either water or alcohol at a temperature from about 70° to 100° C. to yield the imidazolidone of formula V. It is generally found in the case of IVb with R equal to $COR_3$ that the $COR_3$ group is also hydrolyzed in this step to give V and R equal to hydrogen.

The imidazolidone of formula V (wherein $R_2$ is as defined for Compound IV above) is heated in an inert solvent (such as toluene, xylene or cyclohexane) at a temperature from about 80° to about 200° C. in the presence of a reagent (such as phosphorus pentasulfide) capable of substituting sulfur for oxygen to yield the imidazolidinethione of formula VI and some of the compound of formula VII (as a free base). In the case of formula V compounds wherein R is hydrogen, reaction with phosphorus pentasulfide also affects the free hydroxyl group, altering it to form a sulfur-containing group which may or may not also contain phosphorus. This altered group is nonetheless capable of undergoing ring closure in the final step to form compounds of formula VII. In the case of formula V compounds wherein R is the COR₃ moiety, it is frequently found that the COR₃ group reacts with the thiating reagent (e.g., phosphorus pentasulfide) to form the CSR₃ group. This does not affect the ability of the formula VI compounds in which this change has occured to ring close to the useful compounds of formula VII.

The imidazolidinethione of formula VI (wherein R₂ is as defined for Compound IV above) is heated with HY, wherein Y is a pharmaceutically acceptable anion (such as chloride, fluoride, iodide, bisulfate, p-toluene sulfonate) in a solvent at a temperature from about 0° to about 200° C. to yield the compound of formula VI. The compound of this formula III wherein R is an acyl group may also be made as follows:

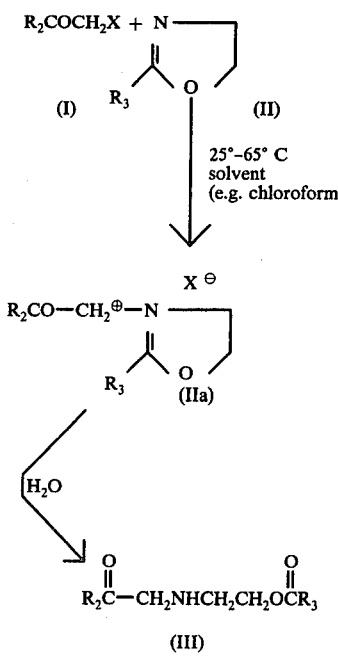

Some of the novel compounds of this invention can be described by the formula:

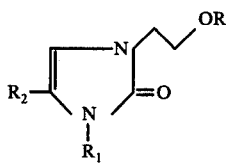

wherein R is selected from the group consisting of hydrogen, $C_1$–$C_6$ alkyl, halo $C_1$–$C_6$ alkyl, phenyl, phenyl substituted with up to three groups selected from the group consisting of $C_1$–$C_6$ alkyl, halo and lower alkoxy and a moiety of the formula COR₃, wherein R₃ is selected from the group consisting of hydrogen, $C_1$–$C_6$ alkyl, $C_1$–$C_6$ alkoxy, phenoxy, halo $C_1$–$C_6$ alkyl, phenyl, and phenyl substituted with up to four group selected from the group consisting of $C_1$–$C_6$ alkyl, halo, trifluoromethyl and $C_1$–$C_6$ alkoxy; R₁ is selected from the group consisting of hydrogen and a moiety of the formula COR₄, wherein R₄ is selected from the group consisting of $C_1$–$C_6$ alkyl, $C_1$–$C_6$ alkoxy, phenoxy, $C_5$–$C_{10}$ cycloalkyl, phenyl, and phenyl or phenoxy substituted with up to four groups selected from the group consisting of $C_1$–$C_6$ alkyl, $C_1$–$C_6$ alkoxyl, halo and trifluoromethyl; and R₂ is selected from the group consisting of phenyl and phenyl substituted with up to two groups selected from the group consisting of $C_1$–$C_6$ alkyl, $C_1$–$C_6$ alkoxy, halo, and trifluoromethyl.

A preferred embodiment of the present invention are the compounds of the above shown formula, wherein R is selected from the group consisting of hydrogen, $C_1$–$C_6$ alkyl, phenyl and a moiety of the formula COR₃; wherein R₃ is selected from the group consisting of hydrogen, $C_1$–$C_6$ alkyl and phenyl; R₁ is selected from the group consisting of hydrogen and a moiety of the formula COR₄, wherein R₄ is selected from the group consisting of $C_1$–$C_6$ alkyl, $C_1$–$C_6$ alkoxyphenyl, $C_5$–$C_6$ cycloalkyl, phenyl and trifluoromethylphenyl; and R₂ is selected from the group consisting of phenyl, and m-halophenyl.

A most preferred embodiment of the present invention are compounds of the above shown formula, wherein R is selected from the group consisting of hydrogen, $C_1$–$C_4$ alkyl, phenyl, and a moiety of the formula COR₃, wherein R₃ is selected from the group consisting of hydrogen, $C_1$–$C_6$ alkyl and phenyl; R₁ is selected from the group consisting of hydrogen and a moiety of the formula COR₄, wherein R₄ is selected from the group consisting of $C_1$–$C_4$ alkyl, phenyl, $C_1$–$C_4$ alkoxyphenyl and trifluoromethylphenyl; and R₂ is phenyl.

Some of the novel compounds of this invention can be described by the formula:

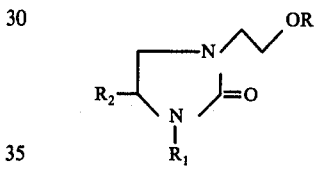

wherein R is selected from the group consisting of hydrogen, $C_1$–$C_6$ alkyl, halo $C_1$–$C_6$ alkyl, phenyl, phenyl substituted with up to three groups selected from the group consisting of $C_1$–$C_6$ alkyl, halo and $C_1$–$C_6$ alkoxy and a moiety of the formula COR₃, wherein R₃ is selected from the group consisting of hydrogen, $C_1$–$C_6$ alkyl, $C_1$–$C_6$ alkoxy, phenoxy, halo $C_1$–$C_6$ alkyl, phenyl, and phenyl or phenoxy substituted with up to four groups selected from the group consisting of $C_1$–$C_6$ alkyl, halo, trifluoromethyl and $C_1$–$C_6$ alkoxy; R₁ is selected from the group consisting of hydrogen and a moiety of the formula COR₄, wherein R₄ is selected from the group consisting of $C_1$–$C_6$ alkyl, $C_1$–$C_6$ alkoxy, phenoxy, $C_5$–$C_{10}$ cycloalkyl, phenyl, and phenyl or phenoxy substituted with up to four groups selected from the group consisting of $C_1$–$C_6$ alkyl, $C_1$–$C_6$ alkoxyl, halo and trifluoromethyl; and R₂ is selected from the group consisting of phenyl and phenyl substituted with up to two groups selected from the group consisting of $C_1$–$C_6$ alkyl, $C_1$–$C_6$ alkoxy, halo and trifluoromethyl.

A preferred embodiment of the present invention are the compounds of the above shown formula, wherein R is selected from the group consisting of hydrogen, $C_1$–$C_6$ alkyl, phenyl and a moiety of the formula COR₃, wherein R₃ is selected from the group consisting of hydrogen, $C_1$–$C_6$ alkyl and phenyl; R₁ is selected from the group consisting of hydrogen and a moiety of the formula COR₄, wherein R₄ is selected from the group consisting of $C_1$–$C_6$ alkyl, $C_1$–$C_6$ alkoxyphenyl, $C_5$–$C_6$ cycloalkyl, phenyl and trifluoromethylphenyl; and R₂ is selected from the group consisting of phenyl and m- halophenyl. An example of such compounds is 1-(2-methoxyethyl)-4-(3-bromophenyl)-2-imidazolidone.

A most preferred embodiment of the present invention are compounds of the above shown formula, wherein R is selected from the group consisting of hydrogen, $C_1$–$C_4$ alkyl, phenyl, and a moiety of the formula $COR_3$, wherein $R_3$ is selected from the group consisting of hydrogen, $C_1$–$C_6$ alkyl, and phenyl; $R_1$ is selected from the group consisting of hydrogen and a moiety of the formula $COR_4$, wherein $R_4$ is selected from the group consisting of $C_1$–$C_4$ alkyl, phenyl, $C_1$–$C_4$ alkoxyphenyl and trifluoromethylphenyl; and $R_2$ is phenyl. An example of such compounds is 1-(2-butoxyethyl)-3-acetyl-4-phenyl-3-imidazolidone.

Some of the novel compounds of this invention can be described by the formula:

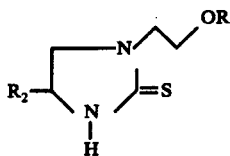

wherein R is selected from the group consisting of $C_1$–$C_6$ alkyl, halo $C_1$–$C_6$ alkyl, phenyl, phenyl substituted with up to three groups selected from the group consisting of $C_1$–$C_6$ alkyl, halo and $C_1$–$C_6$ alkoxy; and $R_2$ is selected from the group consisting of phenyl and phenyl substituted with up to two groups selected from the group consisting of $C_1$–$C_6$ alkyl, halo, $C_1$–$C_6$ alkoxy, and trifluoromethyl.

A preferred embodiment of the present invention are the compounds of the above shown formula, wherein R is selected from the group consisting of $C_1$–$C_6$ alkyl and phenyl; and $R_2$ is selected from the group consisting of phenyl and m-halophenyl.

A most preferred embodiment of the present invention are compounds of the above shown formula, wherein R is selected from the group consisting of $C_1$–$C_4$ alkyl and phenyl; and $R_2$ is phenyl. An example of such compounds is 1-(2-butoxyethyl)-4-phenyl-imidazolidine-2-thione.

Still other novel compounds of the present invention may be illustrated by the formula:

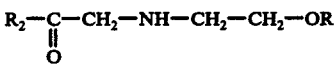

wherein R is selected from the group consisting of hydrogen, $C_1$–$C_6$ alkyl, halo $C_1$–$C_6$ alkyl, phenyl, phenyl substituted with up to three groups selected from the group consisting of lower alkyl, halo, and lower alkoxy, and $COR_3$, wherein $R_3$ is selected from the group consisting of hydrogen, $C_1$–$C_6$ alkyl, halo $C_1$–$C_6$ alkyl, $C_1$–$C_6$ alkoxy, phenoxy, phenyl and phenyl or phenoxy substituted with up to four groups selected from the group consisting of lower alkyl, halo, lower alkoxy, and trifluoromethyl; and $R_2$ is selected from the group consisting of phenyl and phenyl substituted with up to two groups selected from the group consisting of halo, lower alkoxy, lower alkyl, and trifluoromethyl.

A preferred embodiment of the present invention are compounds of the above shown formula, wherein R is selected from the group consisting of hydrogen, $C_1$–$C_6$ alkyl, phenyl, and $COR_3$, wherein R is selected from the group consisting of hydrogen, $C_1$–$C_6$ alkyl and phenyl; and $R_2$ is selected from the group consisting of phenyl, and m-halophenyl.

A most preferred embodiment of the present invention are compounds of the above shown formula wherein R is selected from the group consisting of hydrogen, $C_1$–$C_4$ alkyl, phenyl and $COR_3$, wherein $R_3$ is selected from the group consisting of hydrogen, $C_1$–$C_6$ alkyl and phenyl; and $R_2$ is phenyl.

EXAMPLE 1

1-(2-Methoxyethyl)-4-phenyl-4-imidazolin-2-one

Phenacyl bromide (60 g.), in 200 ml. of methylene chloride, is added over one hour to 2-methoxyethylamine (52 g.), in 100 ml. of methylene chloride, and cooled with an ice bath. The mixture is stirred for two hours at 0° C. Water (400 ml.) is added and the organic layer is separated, dried over anhydrous sodium sulfate and concentrated under aspirator vacuum (at room temperature). The viscous oil (260 g.) is dissolved in methanol (200 ml.), cooled to 0° C. and acetic acid (80 ml.) and potassium cyanate (30 g.) is added. The mixture is refluxed for 90 minutes, the solvent removed under reduced pressure and the residue is taken up in 600 ml. of chloroform and washed with saturated sodium bicarbonate solution. The chloroform layer is washed, dried over sodium sulfate and concentrated to give a semisolid. Trituration with ether and filtration yields the title product as a yellow crystal; m.p. 152°–153° C.

EXAMPLE 2

1-(2-methoxyethyl)-4-phenyl-4-imidazolin-2-one

Phenacyl bromide (199 g.), in 400 ml. of chloroform, is added over one half hour to a mixture of 2-methoxyethylamine (82 g) and triethylamine (152 g.) in 200 ml. of chloroform at 0° C. The mixture is stirred for two hours at 0°–10° C. Water (400 ml.) is added and the organic layer is separated and washed with another 400 ml. of water. The chloroform layer is cooled to 0° C. with an ice bath and glacial acetic acid (72 g.) potassium cyanate (89 g.) and methanol (100 ml.) are added. The mixture is refluxed for ninety minutes, cooled and washed with saturated sodium bicarbonate solution, and the organic layer is dried over anhydrous sodium sulfate and then concentrated to give a semisolid. Trituration with 300 ml. of ether and filtration gives the title product as a yellow crystal; m.p. 152°–154° C.

EXAMPLE 3

1-(2-methoxyethyl)-4-phenyl-2-imidazolidone

Approximately 10.9 g. of 1-(2-methoxyethyl)-4-phenyl-4-imidazolin-2-one and 1 g. of 10% palladium on carbon in 100 ml. of ethanol is hydrogenated in a Parr Shaker apparatus at 30 psig of hydrogen for 45 minutes. The catalyst is filtered, washed with ethanol, and the filtrate is concentrated to give the title compound as a waxy white solid; m.p. 82°–83° C.

The above reduction can also be carried out with acetic acid as the solvent, and at atmospheric pressure in either solvent.

EXAMPLE 4

1-(2-methoxyethyl)-4-phenylimidazolidine-2-thione

Approximately 1 g. of 1-(2-methoxyethyl)-4-phenyl-2-imidazolidone and 0.4 g. of phosphorous pentasulfide are refluxed in toluene overnight (16 hours). The toluene is distilled off under reduced pressure and the residual semisolid is dissolved in a solution of 50 ml. of chloroform and 30 ml. of 20% sodium hydroxide. The organic layer is separated, washed, dried and the solvent removed to give 1 g. of an oil. The oil is dissolved in 3 ml. of acetone and anhydrous hydrogen chloride is bubbled in for two minutes. The precipitated tetramisole hydrochloride is filtered off and the filtrate concentrated to dryness. The filtrate is recrystallized from benzene-cyclohexane to yield the title compound as a white solid; m.p. 76°–78° C.

EXAMPLE 5

Preparation of tetramisole hydrochloride from 1-(2-methoxyethyl)-4-phenylimidazolidine-2-thione Approximately 236 mg. of 1-(2-methoxyethyl)-4-phenylimidazolidine-2-thione, 5 ml. of concentrated hydrochloric acid, and 5 ml. of acetone are refluxed together for one hour. The solution is then concentrated to dryness under reduced pressure and triturated with 2 ml. of ethanol. The white solid precipitate is filtered off to yield the title compound.

EXAMPLE 6

Preparation of tetramisole hydrochloride from 1-(2-methoxyethyl)-4-phenyl-2-imidazolidone Approximately 4.4 g. of 1-(2-methoxyethyl)-4-phenyl-2-imidazolidone and 2 g. of phosphorus pentasulfide are refluxed together in 200 ml. of toluene for 20 hours. The toluene is distilled off under reduced pressure and the residue is taken in 100 ml. of chloroform and washed with 50 ml. of 20 percent sodium hydroxide solution. The organic layer is washed with water, dried and the solvent removed to give a yellow oil. The oil is refluxed for one hour in a solution of 10 ml. of concentrated hydrochloric acid and 10 ml. of ethanol. The solution is concentrated to dryness, the residual semisolid triturated with ethanol (20 ml.), filtered and dried to yield the title compound; m.p. 260°–262° C.

EXAMPLE 7

1-(2-hydroxyethyl)-4-phenyl-4-imidazolin-2-one

Phenacyl bromide (60 g.), in methylene chloride (100 ml.), is added over a period of 30 minutes to monoethanol amine (41 g.) in methylene chloride (100 ml.). The solution is cooled to 0° C. with an ice bath, stirred for another 90 minutes at 0°–5° C., and then 400 ml. of water is added. The organic layer is separated, dried over anhydrous sodium sulfate, and concentrated under reduced pressure at approximately room temperature. The residual oil is dissolved in methanol (150 ml.), cooled, and a solution of sodium cyanate (24 g.) in acetic acid (30 ml.) is added. The mixture is refluxed for one hour and then cooled. The white solid precipitate is filtered, washed with water, methanol and then dried to yield the title product; m.p. 203°–205° C.

EXAMPLE 8

1-(2-hydroxyethyl)-4-phenyl-2-imidazolidone

A slurry of 1-(2-hydroxyethyl)-4-phenyl-4-imidazolin-2-one (10.2 g.) and 10 percent palladium on carbon (1 g.) in ethanol (200 ml.) is hydrogenated in a Parr Shaker apparatus at approximately 30 psig of hydrogen for three hours. The catalyst is then filtered, washed with ethanol, and the combined filtrate and washings are concentrated to give a colorless oil which solidifies on standing to yield the title compound; m.p. 60°–63° C.

EXAMPLE 9

Preparation of tetramisole hydrochloride from 1-(2-hydroxyethyl)-4-phenyl-2-imidazolidone A mixture of 1-(2-hydroxyethyl)-4-phenyl-2-imidazolidone (4.1 g.) and phosphorous pentasulfide (1.8 g.) in toluene (25 ml.) is refluxed for twenty hours. The toluene is distilled off under reduced pressure and the residue is dissolved in a solution of chloroform (50 ml.) and 20 percent sodium hydroxide (50 ml). The organic layer is separated, washed, dried over sodium sulfate and concentrated to an oil. The oil is refluxed and a solution of ethanol (10 ml.) and concentrated hydrochloric acid (20 ml.) for one hour. The solution is concentrated to dryness, triturated with ethanol (20 ml.), and filtered to yield the title compound as a white solid; m.p. 260° C.

EXAMPLE 10

1-(2-Acetoxyethyl)-4-phenyl-2-imidazolidone

Approximately 9.2 g of 1-(2-hydroxyethyl-4-phenyl-2-imidazolidone is stirred with acetic anhydride (25 ml.) and p-toluenesulfonic acid (200 mg.) for four hours, during which time the imidazolidone completely dissolves. The solution (100 ml.) from which a white solid precipitates. The solid is extracted with methylene chloride (3 × 100 ml.). The organic layer is separated, dried and the solvent removed to give a pale yellow solid. Recrystallization from ether gives the title compound as a white crystalline solid; m.p. 88°–90° C.

EXAMPLE 11

Preparation of tetramisole hydrochloride from 1-(2-acetoxyethyl)-4-phenyl-2-imidazolidone Approximately 5 g. of 1-(2-acetoxyethyl)-4-phenyl-2-imidazolidone and 1.8 g. of phosphorous pentasulfide is refluxed in 20 ml. of toluene for twenty hours. The solvent is distilled off under reduced pressure and the residue is dissolved in a solution of chloroform (100 ml.) and 20 percent sodium hydroxide (100 ml.). The organic layer is then separated, washed, dried over sodium sulfate treated with charcoal, filtered and concentrated to an oil. The oil is refluxed in a solution of concentrated hydrochloric acid (20 ml.) and ethanol (10 ml.) for one hour. The solution is concentrated to dryness and the residue triturated with ethanol (20 ml.) and then filtered to yield the title compound with a tan coloration; m.p. 258°–260° C.

EXAMPLE 12

1-(2-acetoxyethyl)-4-phenyl-4-imidazolin-2-one

Approximately 9 g. of 2-methyloxazoline and 20 g. of phenacyl bromide is refluxed in 100 ml. of chloroform for one hour. The solvent is concentrated under reduced pressure and acetic acid (10 ml.), potassium cyanate (9 g.), and methanol (100 ml.) is added to the residual oil and the mixture refluxed for one hour. The methanol is removed under reduced pressure and the residue taken up in 200 ml. of methylene chloride and washed with saturated sodium bicarbonate solution. The organic layer is dried and concentrated to a semisolid. Recrystallization from benzene-cyclohexane yields the title compound; m.p. 120°–122° C.

EXAMPLE 13

Reduction of 1-(2-acetoxyethyl)-4-phenyl-4-imidazolin-2-one

Approximately 1 g. of 1-(2-acetoxyethyl)-4-phenyl-4-imidazolin-2-one and 250 mg. of 10% palladium on carbon in 10 ml. of ethanol is stirred in an atmosphere of hydrogen. After about three-quarters of an hour the catalyst is filtered and washed with 20 ml. of ethanol. The combined filtrates are concentrated to yield the title compound as a white solid; m.p. 86°–88° C.

EXAMPLE 14

1-(2-methoxyethyl)-3-acetyl-4-phenyl-4-imidazolin-2-one

Approximately 21.8 g of 1-(2-methoxyethyl)-4-phenyl-4-imidazolin-2-one and 120 ml. of acetic anhydride is refluxed together for four hours. The acetic anhydride is distilled out at reduced pressure. The residual semisolid is recrystallized from ether to yield the title compound as a white solid; m.p. 73°–75° C.

EXAMPLE 15

Racemic 1-(2-methoxyethyl)-3-acetyl-4-phenyl-2-imidazolidone

Approximately 3.9 g. of 1-(2-methoxyethyl)-3-acetyl-4-phenyl-4-imidazolin-2-one and 400 mg. of 10% palladium on carbon in 30 ml. of ethanol is hydrogenated in the Parr Shaker apparatus at 30 psig of hydrogen. After one hour the catalyst is filtered and washed with 50 ml. of ethanol. The combined filtrate is concentrated to yield the title compounds as a colorless oil.

EXAMPLE 16

Hydrolysis of 1-(2-methoxyethyl)-3-acetyl-4-phenyl-2-imidazolidone to 1-(2-methoxyethyl)-4-phenyl-2-imidazolidone Approximately 2.6 g. of the 3 acetyl derivative is refluxed in 20 ml. of 10 percent sodium hydroxide for one hour. The solution is cooled and then extracted with chloroform (2×20 ml.). The combined chloroform extract is washed, dried over sodium sulfate and concentrated to give the title compound as a solid; m.p. 81°–83° C.

EXAMPLE 17

1-(2-methoxyethyl)-3-benzoyl-4-phenyl-4-imidazolin-2-one

Approximately 4.36 g. of 1-(2-methoxyethyl)-4-phenyl-4-imidazolin-2-one, 3 g. of triethylamine and 3 g. of benzoyl chloride are refluxed together for three hours in chloroform. The solution is cooled, washed with water, dried and the solvent removed to give an oil which is the O-benzoyl ester. The ester is refluxed for three hours in 20 ml. of xylene. The xylene is removed at reduced pressure. Recrystallization from ether gives the title compound as a pale yellow solid; m.p. 112°–117° C.

EXAMPLE 18

1-(2-methoxyethyl)-3-benzoyl-4-phenyl-4-imidazolin-2-one

Approximately 21.8 g. of 1-(2-methoxyethyl)-4-phenyl-4-imidazolin-2-one, 14.5 g. of benzoyl chloride and 20 g. of tri-n-butylamine are refluxed together in 60 ml. of xylene for sixteen hours. The solvent is distilled off under reduced pressure and the remaining viscous oil is dissolved in 300 ml. of benzene. The benzene solution is washed with water (2×100 ml.), dried over sodium sulfate, and the solvent removed to give a semisolid. Recrystallization from ether gives the title compound as a pale yellow solid; m.p. 114°–117° C.

EXAMPLE 19

Preparation of other 1-(2-methoxyethyl)-3-acyl-4-phenyl-4-imidazolin-2-ones

The following acyl derivatives are prepared by procedures identical to that described for the N-benzoyl derivative of Example 18:

(a) 1-(2-methoxyethyl)-3-cyclohexanecarbonyl-4-phenyl-4-imidazolin-2-one;
(b) 1-(2-methoxyethyl)-3-p-trifluoromethylbenzoyl-4-phenyl-4-imidazolin-2-one;
(c) 1-(2-methoxyethyl)-3-(1-adamantanecarbonyl)-4-phenyl-4-imidazolin-2-one;
(d) 1-(2-methoxyethyl)-3-o-anisoyl-4-phenyl-4-imidazolin-2-one;
(e) 1-(2-methoxyethyl)-3-(2-chlorobenzoyl)-4-phenyl-4-imidazolin-2-one;
(f) 1-(2-methoxyethyl)-3-(2,4-dichlorobenzoyl)-4-phenyl-4-imidazolin-2-one; and
(g) 1-(2-methoxyethyl)-3-(2-methylbenzoyl)-4-phenyl-4-imidazolin-2-one.

EXAMPLE 20

Hydrogenations of 3-acyl derivatives of 1-(2-methoxyethyl)-4-phenyl-4-imidazolin-2-one The 3-acyl-1-(2-methoxyethyl)-4-phenyl-4-imidazolin-2-one and 10% palladium or carbon catalyst is taken in ethanol and hydrogenated in a Parr Shaker at 30–50 psig hydrogen from about 30 minutes to about 6 hours. The catalyst is then filtered and the filtrate concentrated to give a 1-(2-methoxyethyl)-3-acyl-2-imidazolidones. The following compounds are prepared in the above described manner:

(a) 1-(2-methoxyethyl)-3-benzoyl-4-phenyl-2-imidazolidone;
(b) 1-(2-methoxyethyl)-3-cyclohexanecarbonyl-4-phenyl-2-imidazolidone;
(c) 1-(2-methoxyethyl)-3-p-trifluoromethylbenzoyl-4-phenyl-2-imidazolidone;
(d) 1-(2-methoxyethyl)-3-o-anisoyl-4-phenyl-2-imidazolidone;
(e) 1-(2-methoxyethyl)-3-(1-adamantanecarbonyl)-4-phenyl-2-imidazolidone;
(f) 1-(2-methoxyethyl)-3-(2-chlorobenzoyl)-4-phenyl-2-imidazolidone;
(g) 1-(2-methoxyethyl)-3-(2,4-dichlorobenzoyl)-4-phenyl-2-imidazolidone; and
(h) 1-(2-methoxyethyl)-3-(2-methylbenzoyl)-4-phenyl-2-imidazolidone.

EXAMPLE 21

1-(2-butoxyethyl)-4-phenyl-4-imidazolin-2-one

Phenacyl bromide (10 g.) in 50 ml of chloroform is added over 20 minutes to a mixture of 2-butoxyethylamine (6 g.) and triethylamine (7 g.) in 50 ml. of chloroform at 0° C. The mixture is stirred for 2 hours. Water (100 ml.) is added, the organic layer separated, cooled to 0° C. and glacial acetic acid (5 ml.), potassium cyanate (5 g.) and methanol (20 ml.) are added. The mixture is refluxed for ninety minutes, cooled, washed with saturated sodium bicarbonate solution, dried, and solvent removed to give the title product.

EXAMPLE 22

1-(2-butoxyethyl)-4-phenyl-2-imidazolidone

A solution of 1-(2-butoxyethyl)-4-phenyl-4-imidazolin-2-one in ethanol with 10% palladium or carbon catalyst is reduced in an atmosphere of hydrogen. After the theoretical amount of hydrogen is absorbed, the catalyst is filtered and filtrate concentrated to give the title compound.

EXAMPLE 23

1-(2-methoxyethyl)-4-(2-chlorophenyl)-4-imidazolin-2-one

To o-chlorophenacyl bromide (23.4 g.) in 100 ml. of chloroform is added over 30 minutes 2-methoxyethylamine (20 g.) in 100 ml. of chloroform which is cooled with an ice bath. The mixture is stirred for an additional hour at 0° C. Water (200 ml.) is added and the organic layer is separated, cooled to 0° C. with an ice bath and then glacial acetic acid (8 ml.), potassium cyanate (9 g.) and methanol are added. The mixture is refluxed for 90 minutes, cooled, washed with saturated sodium bicarbonate solution, dried over anhydrous sodium sulfate and solvent removed to give the title product.

EXAMPLE 24

1-(2-methoxyethyl)-4-(substituted phenyl)-4-imidazolin-2-ones

The following 1-(2-methoxyethyl)-4-(substituted phenyl)-4-imidazolin-2-ones are prepared in an identical manner to that described in Example 23:

(a)  1-(2-methoxyethyl)-4-(2,4-dichlorophenyl)-4-imidazolin-2-one and
(b)  1-(2-methoxyethyl)-4-(p-trifluoromethylphenyl)-4-imidazolin-2-one.

EXAMPLE 25

Preparation of 1-(2-methoxyethyl)-4-(substituted phenyl)-2-imidazolidone

A solution of 1-(2-methoxyethyl)-4-(substituted phenyl)-4-imidazolin-2-one in ethanol with 10% palladium on carbon catalyst is reduced at from about 15 psig hydrogen to about 1000 psig hydrogen. After theoretical amount of hydrogen is absorbed, the catalyst is filtered and the filtrate is concentrated to give the 1-(2-methoxyethyl)-4-(substituted phenyl)-2-imidazolidones. The following compounds were prepared in the above manner:

(a)  1-(2-methoxyethyl)-4-(m-trifluoromethyl)-2-imidazolidone;
(b)  1-(2-methoxyethyl)-4-(m-methylphenyl)-2-imidazolidone;
(c)  1-(2-methoxyethyl)-4-(p-trifluoromethylphenyl)-2-imidazolidone; and
(d)  1-(2-methoxyethyl)-4-(m-methoxyphenyl)-2-imidazolidone.

EXAMPLE 26

1-(2-benzoyloxyethyl)-4-phenyl-4-imidazolin-2-one

Approximately 15 g. of 2-phenyloxazoline and 20 g. of phenacyl bromide is refluxed in 100 ml. of chloroform for 1 hour. The solvent is concentrated under reduced pressure and acetic acid (10 ml.), potassium cyanate (9 g.) and methanol (100 ml.) are added and the mixture refluxed for 1 hour. The methanol is removed under reduced pressure and the residue taken up in 200 ml. of methylene chloride and washed with saturated sodium bicarbonate solution. The organic layer is dried and concentrated to give the title compound.

EXAMPLE 27

Preparation of other 1-(2-acyloxyethyl)-4-phenyl-4-imidazolin-2-ones

The following 1-(2-acyloxyethyl)-4-phenyl-4-imidazolin-2-ones are prepared by procedures identical to that described for the benzoyloxy derivatives of Example 26:

(a)  1-[2-(propionyloxy)ethyl]-4-phenyl-4-imidazolin-2-one;
(b)  1-[2-(p-methylbenzoyloxy)ethyl]-4-phenyl-4-imidazolin-2-one; and
(c)  1-[2-(p-trifluoromethylbenzoyloxy)ethyl]-4-phenyl-4-imidazolin.

EXAMPLE 28

Preparation of 1-(2-acyloxyethyl)-4-phenyl-2-imidazolidones

The following 1-(2-acyloxyethyl)-4-phenyl-2-imidazolidones are prepared by the catalytic reduction of 1-(2-acyloxyethyl)-4-phenyl-4-imidazolin-2-ones identical to that described for 1-(2-acetoxyethyl) derivatives of Example 13:

(a)  1-[2-benzoyloxyethyl]-4-phenyl-2-imidazolidone;
(b)  1-[2-(propionyloxy)ethyl]-4-phenyl-2-imidazolidone;
(c)  1-[2-(p-methylbenzoyloxy)ethyl]-4-phenyl-2-imidazolidone;
(d)  1-[2-p-trifluoromethylbenzoyloxy)ethyl]-4-phenyl-2-imidazolidone.

EXAMPLE 29

The following amino ketones of Formula A are prepared by the reaction of the corresponding derivatized ethanolamines of their acid addition salts with the corresponding phenacyl bromides as in the first three sentences of Example 2:

$$R_2CCH_2NHCH_2CH_2OR$$
$$\overset{O}{\|}$$
(A)

| $R_2$ | R |
|---|---|
| $C_6H_5$ | $C_2H_5$ |
| $C_6H_5$ | $C_3H_7$-i |
| $C_6H_5$ | $CH_2CH_2Cl$ |
| $C_6H_5$ | $C_6H_5$ |
| $C_6H_5$ | $C_6H_4$—(p-$CH_3$) |
| $C_6H_5$ | $C_6H_4$—(p-Cl) |
| $C_6H_5$ | $C_6H_4$—(p-$OCH_3$) |
| $C_6H_5$ | $C_6H_4$—(m-$OCH_3$) |
| $C_6H_5$ | C (O) $C_2H_5$ |
| $C_6H_5$ | C (O) $C_4H_9$ |
| $C_6H_5$ | C (O) $OCH_3$ |
| $C_6H_5$ | C (O) $OC_6H_5$ |
| m-$OCH_3$—$C_6H_4$ | $CH_3$ |
| m-CL—$C_6H_4$ | H |
| m-Br—$C_6H_4$ | H |
| m-Cl—$C_6H_4$ | C (O) $CH_3$ |
| $C_6H_5$ | C (O) $OC_6H_4$(p-$CH_3$) |
| $C_6H_5$ | C (O) $OC_6H_4$(o-$CH_3$) |
| $C_6H_5$ | C (O) $OC_6H_4$(P-$OCH_3$) |
| $C_6H_5$ | C (O) $C_6H_5$ |
| $C_6H_5$ | C (O) $C_2H_5$ |
| $C_6H_5$ | C (O) $C_4H_9$ |
| $C_6H_5$ | C (O) $OCH_3$ |
| $C_6H_5$ | C (O) $OC_6H_5$ |
| m-$OCH_3$—$C_6H_4$ | $CH_3$ |

-continued $$R_2CCH_2NHCH_2CH_2OR$$
(A)

| $R_2$ | R |
|---|---|
| m-CL—$C_6H_4$ | H |
| m-Br—$C_6H_4$ | H |
| m-Cl—$C_6H_4$ | C(O)$CH_3$ |
| $C_6H_5$ | C(O)O$C_6H_4$(p-$CH_3$) |
| $C_6H_5$ | C(O)O$C_6H_4$(o-$CH_3$) |
| $C_6H_5$ | C(O)O$C_6H_4$(p-O$CH_3$) |
| $C_6H_5$ | C(O)$C_6H_5$ |
| $C_6H_5$ | C(O)$C_6H_4$(p-$CH_3$) |
| $C_6H_5$ | C(O)$C_6H_4$(p-O$CH_3$) |
| $C_6H_5$ | C(O)$C_6H_4$(m-$CF_3$) |
| m-Br—$C_6H_4$ | C(O)$C_6H_5$ |
| m-$CF_3$—$C_6H_4$ | $CH_3$ |
| m-$CH_3$—$C_6H_4$ | $CH_3$ |
| m-Cl—$C_6H_4$ | $C_6H_5$ |
| M-$CF_3$—$C_6H_4$ | C(O)O$CH_3$ |
| P-Cl—$C_6H_4$ | $CH_3$ |
| m-Br—$C_6H_4$ | $C_2H_5$ |

The substituted ethanolamine and their acid addition salts and phenacyl bromide starting materials are proposed by known literature methods.

EXAMPLE 30

The following imidazolinones of Formula B are prepared from aminoketones prepared as in Example 30 by the reaction with potassium cyanate as in Example 1 and 2:

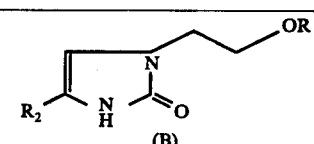
(B)

| $R_2$ | R |
|---|---|
| $C_6H_5$ | $C_2H_5$ |
| $C_6H_5$ | $C_3H_7$-i |
| $C_6H_5$ | $CH_2CH_2Cl$ |
| $C_6H_5$ | $C_6H_5$ |
| $C_6H_5$ | $C_6H_4$(p-$CH_3$) |
| $C_6H_5$ | $C_6H_4$(p-Cl) |
| $C_6H_5$ | $C_6H_4$(p-O$CH_3$) |
| $C_6H_5$ | $C_6H_4$(m-O$CH_3$) |
| $C_6H_5$ | C(O)$C_2H_5$ |
| $C_6H_5$ | C(O)$C_4H_9$ |
| $C_6H_5$ | C(O)O$CH_3$ |
| $C_6H_5$ | C(O)O$C_6H_5$ |
| $C_6H_5$ | C(O)O$C_6H_4$(p-$CH_3$) |
| $C_6H_5$ | C(O)O$C_6H_4$(o-$CH_3$) |
| $C_6H_5$ | C(O)O$C_6H_4$(p-O$CH_3$) |
| $C_6H_5$ | C(O)$C_6H_5$ |
| $C_6H_5$ | C(O)$C_6H_5$(p-$CH_3$) |
| $C_6H_5$ | C(O)$C_6H_4$(p-O$CH_3$) |
| $C_6H_5$ | C(O)$C_6H_4$(m-$CF_3$) |
| m-Br—$C_6H_4$ | C(O)$C_6H_5$ |
| m-$CF_3$—$C_6H_4$ | $CH_3$ |
| m-$CH_3$—$C_6H_4$ | $CH_3$ |
| m-O$CH_3$—$C_6H_4$ | $CH_3$ |
| m-Cl—$C_6H_4$ | H |
| m-Br—$C_6H_4$ | H |
| m-Cl—$C_6H_4$ | C(O)$CH_3$ |
| m-Cl—$C_6H_4$ | $C_6H_5$ |
| m-$CF_3$—$C_6H_4$ | C(O)O$CH_3$ |
| p-Cl—$C_6H_4$ | $CH_3$ |
| m-Br—$C_6H_4$ | $C_2H_5$ |

EXAMPLE 31

The following 3-substituted imidazolinones of Formula C are prepared as in Example 18 using the appropriate carbonyl halides or anhydrides and the corresponding 3-H-imidazolinones:

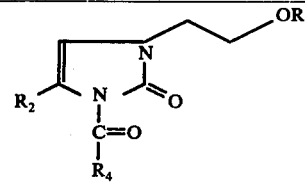
(C)

| $R_2$ | R | $R_4$ |
|---|---|---|
| $C_6H_5$ | $C_2H_5$ | $CH_3$ |
| $C_6H_5$ | $C_3H_7$-i | $C_6H_5$ |
| $C_6H_5$ | $CH_2CH_2Cl$ | $CH_3O$ |
| $C_6H_5$ | $C_6H_5$ | $C_6H_5O$ |
| $C_6H_5$ | $C_6H_4$(p-$CH_3$) | $CH_3$ |
| $C_6H_5$ | $C_6H_4$(p-Cl) | ⬡ |
| $C_6H_5$ | $C_6H_4$(p-O$CH_3$) | $C_6H_5$ |
| $C_6H_5$ | $C_6H_4$(m-O$CH_3$) | $C_2H_5$ |
| $C_6H_5$ | C(O)$C_2H_5$ | $CH_3$ |
| $C_6H_5$ | C(O)$C_4H_9$ | $C_6H_4$(p-$CH_3$) |
| $C_6H_5$ | CH$_{OCH_3}$ | $CH_3$ |
| $C_6H_5$ | C(O)O$C_6H_5$ | $C_2H_5$ |
| $C_6H_5$ | C(O)O$C_6H_4$(p-$CH_3$) | $C_6H_3$(2,4-di-$CH_3$) |
| $C_6H_5$ | C(O)O$C_6H_4$(o-O$CH_3$) | $CH_3$ |
| $C_6H_5$ | C(O)O$C_6H_4$(p-O$CH_3$) | $C_3H_7$ |
| $C_6H_5$ | C(O)$C_6H_5$ | $C_2H_5O$ |
| $C_6H_5$ | C(O)$C_6H_4$(p-$CH_3$) | ⬡ |
| $C_6H_5$ | C(O)$C_6H_4$(p-O$CH_3$) | $C_6H_4$(p-$CF_3$) |
| $C_6H_5$ | C(O)$C_6H_4$(m-$CF_3$) | $C_6H_4$O(P-$CH_3$) |
| m-Br—$C_6H_4$ | C(O)$C_6H_5$ | $C_4H_9O$ |
| m-$CF_3$—$C_6H_4$ | $CH_3$ | $C_6H_4$(p-O$CH_3$) |
| m-$CH_3$—$C_6H_4$ | $CH_3$ | $CH_3$ |
| m-$CH_3O$—$C_6H_4$ | $CH_3$ | i-$C_3H_7$ |
| m-Cl=$C_6H_4$ | H | $C_6H_5$ |
| m-Br—$C_6H_4$ | H | $C_6H_4$(m-Cl) |
| m-Cl—$C_6H_4$ | C(O)$CH_3$ | $C_6H_4$(p-$CH_3O$) |
| m-Cl—$C_6H_4$ | $C_6H_5$ | $C_6H_4$(p-$CH_3$)O |
| m-$CF_3$—$C_6H_4$ | C(O)O$CH_3$ | $CH_3$ |
| p-Cl—$C_6H_4$ | $CH_3$ | $C_4H_9OC(O)$ |
| m-Br—$C_6H_4$ | $C_2H_6$ | $C_6H_5$ |

EXAMPLE 32

The following 3-substituted imidazolidones of Formula D are prepared by catalytic hydrogenation of the corresponding 3-substituted imidazolinony using the procedure of Example 13:

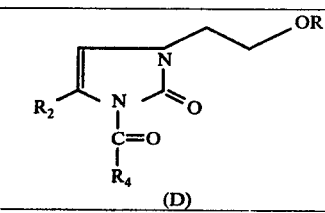
(D)

| $R_2$ | R | $R_4$ |
|---|---|---|
| $C_6H_5$ | $C_2H_5$ | $CH_3$ |
| $C_6H_5$ | $C_3H_7$-i | $C_6H_5$ |
| $C_6H_5$ | $C_2H_5$ | $CH_3O$ |
| $C_6H_5$ | $C_6H_5$ | $C_6H_5O$ |
| $C_6H_5$ | $C_6H_4$(p-$CH_3$) | $CH_3$ |
| $C_6H_5$ | $C_6H_5$ | ⬡ |
| $C_6H_5$ | $C_6H_4$(p-O$CH_3$) | $C_6H_5$ |
| $C_6H_5$ | $C_6H_4$(m-O$CH_3$) | $C_2H_5$ |
| $C_6H_5$ | C(O)$C_2H_5$ | $CH_3$ |
| $C_6H_5$ | C(O)$C_4H_9$ | $C_6H_4$(p-$CH_3$) |
| $C_6H_5$ | C(O)O$CH_3$ | $CH_3$ |
| $C_6H_5$ | C(O)$C_6H_5$ | $C_2H_5$ |
| $C_6H_5$ | C(O)O$C_6H_4$(p-$CH_3$) | $C_6H_3$(2,4-di-$CH_3$) |
| $C_6H_5$ | C(O)O$C_6H_4$(o-$CH_3$) | $CH_3$ |
| $C_6H_5$ | C(O)O$C_6H_4$(p-O$CH_3$) | $C_3H_7$ |
| $C_6H_5$ | C(O)$C_6H_5$ | $C_2H_5O$ |
| $C_6H_5$ | C(O)$C_6H_4$(p-$CH_3$) | ⬡ |

-continued

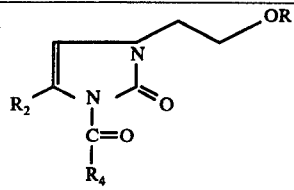

(D)

| R₂ | R | R₄ |
|---|---|---|
| C₆H₅ | C(O)C₆H₄(p-OCH₃) | C₆H₄(p-CF₃) |
| C₆H₅ | C(O)C₆H₄(m-CF₃) | C₆H₄O(p-CH₃) |
| m-CF₃C₆H₄ | CH₃ | C₆H₄(p-OCH₃) |
| m-CH₃C₆H₄ | CH₃ | CH₃ |
| m-CH₃O—C₆H₄ | CH₃ | i-C₃H₇ |
| m-CF₃—C₆H₄ | C(O)OCH₃ | CH₃ |

In the corresponding Formula C compounds are hydrogenated in the presence of a homogeneous hydrogenation catalyst such as tristriphenylphosphino chlororhodium, the following compounds of Formula D are prepared:

| R₂ | R | R₄ |
|---|---|---|
| m-Br-C₆H₄ | C(O)C₆H₅ | C₄H₉O |
| m-Cl-C₆H₄ | H | C₆H₅ |
| m-Br-C₆H₄ | H | C₆H₄(m-Cl) |
| m-Cl-C₆H₄ | C(O)CH₃ | C₆H₄(p-CH₃O) |
| m-Cl-C₆H₄ | C₆H₅ | C₆H₄(p-CH₃)O |
| p-Cl-C₆H₄ | CH₃ | C₄H₉OC(O) |
| m-Br-C₆H₄ | C₂H₄ | C₆H₅ |

EXAMPLE 33

The following imidazolidones of Formula E are prepared by hydrogenation of the corresponding 3-unsubstituted imidazolinones according to the procedure of Example 3:

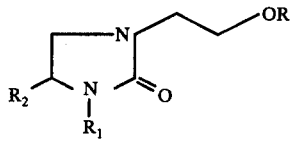

(E)

| R₂ | R |
|---|---|
| C₆H₅ | C₂H₅ |
| C₆H₅ | C₃H₇-i |
| C₆H₅ | C₆H₅ |
| C₆H₅ | C₆H₄(p-CH₃) |
| C₆H₅ | C₆H₄(p-OCH₃) |
| C₆H₅ | C₆H₄(m-OCH₃) |
| C₆H₅ | C (O) C₂H₅ |
| C₆H₅ | C (O) C₄H₉ |
| C₆H₅ | C (O) OCH₃ |
| C₆H₅ | C (O) OC₆H₅ |
| C₆H₅ | C (O) OC₆H₄(p-CH₃) |
| C₆H₅ | C (O) OC₆H₄(o-CH₃) |
| C₆H₅ | C (O) C₆H₅ |
| C₆H₅ | C (O) C₆H₄(p-CH₃) |
| C₆H₅ | C (O) C₆H₄(p-OCH₃) |
| C₆H₅ | C (O) C₆H₄(m-CF₃) |
| m-CF₃—C₆H₄ | CH₃ |
| m-CH₃—C₆H₄ | CH₃ |
| m-OCH₃—C₆H₄ | CH₃ |
| m-CF₃—C₆H₄ | C (O) OCH₃ |

All of the above compounds and the following compounds can be prepared by hydrolysis of the corresponding formula D compounds of Example 32.

| R₂ | R |
|---|---|
| C₆H₅ | C₆H₄(p-Cl) |
| C₆H₅ | CH₂CH₂Cl |
| m-Br-C₆H₄ | C(O)C₆H₅ |
| m-Cl-C₆H₄ | H |
| m-Br-C₆H₄ | H |
| m-Cl-C₆H₄ | C(O)CH₃ |
| m-Cl-C₆H₄ | C₆H₅ |
| p-Cl-C₆H₄ | CH₃ |
| m-Br-C₆H₄ | C₂H₅ |

EXAMPLE 34

The following imidazolidine-2-thiones of Formula F are prepared from the corresponding 3-unsubstituted imidazolidones as in Example 4:

(F)

| R₂ | R |
|---|---|
| C₆H₅ | C₂H₅ |
| C₆H₅ | C₃H₇-i |
| C₆H₅ | C₆H₅ |
| C₆H₅ | C₆H₄(p-CH₃) |
| C₆H₅ | C₆H₄(p-Cl) |
| C₆H₅ | CH₂CH₂Cl |
| m-CF₃—C₆H₄ | |
| m-CH₃—C₆H₄ | |
| m-OCH₃—C₆H₄ | |

I claim:

1. A compound of the formula:

wherein R is selected from the group consisting of hydrogen, $C_1$–$C_6$ alkyl, halo $C_1$–$C_6$ alkyl, phenyl, phenyl substituted with up to three groups selected from the group consisting of $C_1$–$C_6$ alkyl, halo and $C_1$–$C_6$ alkoxy and a moiety of the formula $COR_3$, wherein $R_3$ is selected from the group consisting of hydrogen, $C_1$–$D_6$ alkyl, $C_1$–$C_6$ alkoxy, phenoxy, halo $C_1$–$C_6$ alkyl, phenyl, and phenyl or phenoxy substituted with up to four groups selected from the group consisting of $C_1$–$C_6$ alkyl, halo, trifluoromethyl and $C_1$–$C_6$ alkoxy; $R_1$ is selected from the group consisting of hydrogen and a moiety of the formula $COR_4$, wherein $R_4$ is selected from the group consisting of $C_1$–$C_6$ alkyl, $C_1$–$C_6$ alkoxy, phenoxy, $C_5$–$C_{10}$ cycloalkyl, phenyl and phenyl or phenoxy substituted with up to four groups selected from the group consisting of $C_1$–$C_6$ alkyl, $C_1$–$C_6$ alkoxy, halo and trifluoromethyl and $R_2$ is selected from the group consisting of phenyl and phenyl substituted with up to two groups selected from the group consisting of $C_1$–$C_6$ alkyl, $C_1$–$C_6$ alkoxy, halo and trifluoromethyl.

2. A compound according to claim 1, wherein R is selected from the group consisting of hydrogen, $C_1$–$C_6$ alkyl, phenyl and a moiety of the formula $COR_3$, wherein $R_3$ is selected from the group consisting of hydrogen, $C_1$–$C_6$ alkyl and phenyl; $R_1$ is selected from the group consisting of hydrogen and a moiety of the formula $COR_4$, wherein $R_4$ is selected from the group consisting of $C_1-C_6$ alkyl, $C_1-C_6$ alkoxyphenyl, $C_5-C_6$ cycloalkyl, phenyl and trifluoromethylphenyl; and $R_2$ is selected from the group consisting of phenyl and m-halophenyl.

3. A compound according to claim 1, wherein R is selected from the group consisting of hydrogen, $C_1-C_4$ alkyl, phenyl and a moiety of the formula $COR_3$, wherein $R_3$ is selected from the group consisting of hydrogen, $C_1-C_6$ alkyl, and phenyl; $R_1$ is selected from the group consisting of hydrogen and a moiety of the formula $COR_4$, wherein $R_4$ is selected from the group consisting of $C_1-C_4$ alkyl, phenyl, $C_1-C_4$ alkoxyphenyl and trifluoromethylphenyl; and $R_2$ is phenyl.

4. The compound according to claim 1, 1-(2-methoxyethyl)-4-phenyl-2-imidazolidone.

5. The compound according to claim 1, 1-(2-hydroxyethyl)-4-phenyl-2-imidazolidone.

6. The compound according to claim 1, 1-(2-acetoxyethyl)-4-phenyl-2-imidazolidone.

7. The compound according to claim 1, 1-(2-methoxyethyl)-4-(3-methoxyphenyl)-2-imidazolidone.

8. The compound according to claim 1, 1-(2-methoxyethyl)-4-(3-bromophenyl)-2-(imidazolidone.

9. The compound according to claim 1, 1-(2-methoxyethyl)-3-acetyl-4-phenyl-2-imidazolidone.

10. The compound according to claim 1, 1-(2-methoxyethyl)-3-benzoyl-4-phenyl-2-imidazolidone.

11. The compound according to claim 1, 1-(2-methoxyethyl)-3-(2-methoxybenzoyl)-4-phenyl-2-imidazolidone.

12. The compound according to claim 1, 1-(2-methoxyethyl)-3-(4-trifluoromethylbenzoyl)-4-phenyl-2-imidazolidone.

13. The compound according to claim 1, 1-(2-methoxyethyl)-3-(1-adamantanecarbonyl)-4-phenyl-2-imidazolidone.

14. The compound according to claim 1, 1-(2-methoxyet-yl)-3-cyclohexanecarbonyl-4-phenyl-2-imidazolidone.

15. The compound according to claim 1, 1-(2-butoxyethyl)-4-phenyl-2-imidazolidone.

16. The compound according to claim 1, 1-(2-methoxyethyl)-4-(3-trifluoromethyl)phenyl-2-imidazolidone.

17. The compound according to claim 1, 1-(2-methoxyethyl)-4-(3-methylphenyl)-2-imidazolidone.

18. The compound according to claim 1, 1-(2-methoxyethyl)-4-(4-trifluoromethyl)phenyl-2-imidazolidone.

19. The compound according to claim 1, 1-(2-benzoyloxyethyl)-4-phenyl-2-imidazolidone.

20. The compound according to claim 1, 1-(2-butoxyethyl)-3-acetyl-4-phenyl-2-imidazolidone.

21. A compound of the formula:

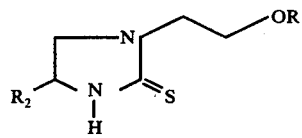

wherein R is selected from the group consisting of $C_1-C_6$ alkyl, halo $C_1-C_6$ alkyl, phenyl, phenyl substituted with up to three groups from the group consisting of $C_1-C_6$ alkyl, halo and $C_1-C_6$ alkoxy; and $R_2$ is selected from the group consisting of phenyl and phenyl substituted with up to two groups selected from the group consisting of $C_1-C_6$ alkyl, $C_1-C_6$ alkoxy, halo and trifluoromethyl.

22. A compound according to claim 21, wherein R is selected from the group consisting of $C_1-C_6$ alkyl and phenyl; and $R_2$ is selected from the group consisting of phenyl and m-halophenyl.

23. A compound according to claim 21, wherein R is selected from the group consisting of $C_1-C_4$ alkyl and phenyl; and $R_2$ is phenyl.

24. The compound according to claim 21, 1-(2-methoxyethyl)-4-phenylimidazolidine-2-thione.

25. The compound according to claim 21, 1-(2-butoxyethyl)-4-phenylimidazolidine-2-thione.

26. The compound according to claim 1, 1-(2-phenoxyethyl)-4-phenylimidazolidine-2-thione.

* * * * *